United States Patent [19]

Huffman

[11] Patent Number: 5,788,490
[45] Date of Patent: Aug. 4, 1998

[54] DENTAL MODEL BASE AND METHOD FOR FORMING STONE DOWELS

[76] Inventor: Ronald E. Huffman, Rte. 1, Box 502M, Sapulpa, Okla. 74066

[21] Appl. No.: 477,541

[22] Filed: Jun. 7, 1995

[51] Int. Cl.$^6$ .................................................. A61C 19/00
[52] U.S. Cl. ................................................. 433/74; 433/213
[58] Field of Search ............................ 433/74, 217, 213

[56] References Cited

U.S. PATENT DOCUMENTS

| | | | |
|---|---|---|---|
| 1,745,570 | 2/1930 | Dimelow | 433/202.1 |
| 1,780,117 | 10/1930 | Craigo . | |
| 2,398,671 | 4/1946 | Saffir . | |
| 2,585,857 | 2/1952 | Schwartz . | |
| 3,453,736 | 7/1969 | Waltke . | |
| 3,518,761 | 7/1970 | Susman et al. . | |
| 3,937,773 | 2/1976 | Huffman . | |
| 3,969,820 | 7/1976 | Kulig et al. . | |
| 4,122,606 | 10/1978 | Roman | 433/74 |
| 4,127,939 | 12/1978 | Samuel et al. . | |
| 4,203,219 | 5/1980 | Wiener | 433/74 |
| 4,240,605 | 12/1980 | Walta | 433/74 |
| 4,242,812 | 1/1981 | Randoll et al. | 433/74 |
| 4,371,339 | 2/1983 | Zeiser | 433/74 |
| 4,382,787 | 5/1983 | Huffman | 433/64 |
| 4,398,884 | 8/1983 | Huffman | 433/74 |
| 4,443,192 | 4/1984 | Blitz | 433/74 |
| 4,449,931 | 5/1984 | Saito | 433/74 |
| 4,459,110 | 7/1984 | Jackson | 433/74 |
| 4,521,188 | 6/1985 | Metzler | 433/74 |
| 4,608,016 | 8/1986 | Zeiser | 433/74 |
| 4,708,835 | 11/1987 | Kiefer | 264/17 |
| 4,721,464 | 1/1988 | Roden et al. | 433/74 |
| 4,767,331 | 8/1988 | Hoe | 433/213 |
| 5,028,235 | 7/1991 | Smith | 433/223 |
| 5,049,075 | 9/1991 | Barrut | 433/196 |
| 5,098,290 | 3/1992 | Honstein et al. | 433/74 |
| 5,197,874 | 3/1993 | Silva et al. | 433/74 |
| 5,207,574 | 5/1993 | Garland | 433/74 |
| 5,352,117 | 10/1994 | Silva | 433/60 |
| 5,393,227 | 2/1995 | Nooning | 433/74 |
| 5,466,152 | 11/1995 | Walker | 433/74 |

FOREIGN PATENT DOCUMENTS 866118   4/1961   United Kingdom .

OTHER PUBLICATIONS

Instruction Booklet, DNA Model & Die System, "Instructions for Use", DVA, Inc.
Instructional Guide, Step by Step, Die–Maker W.O.W. Articulator, Accu Bite, East Lansing, Michigan.
Brochure, "Die–Maker W.O.W. Articulator", Accu Bite.

*Primary Examiner*—Cary E. O'Connor
*Attorney, Agent, or Firm*—Merchant, Gould, Smith, Edell, Welter & Schmidt, P.A.

[57] ABSTRACT

A premanufactured dental model base, and method, for supporting a cast dental model where the dental model base has preformed apertures adaptable for securing the dental model to the dental model base and for disengagably retaining the dental model segment of a damaged tooth. The preformed apertures are adapted to form a stone dowel from the material used to cast the dental model.

16 Claims, 3 Drawing Sheets

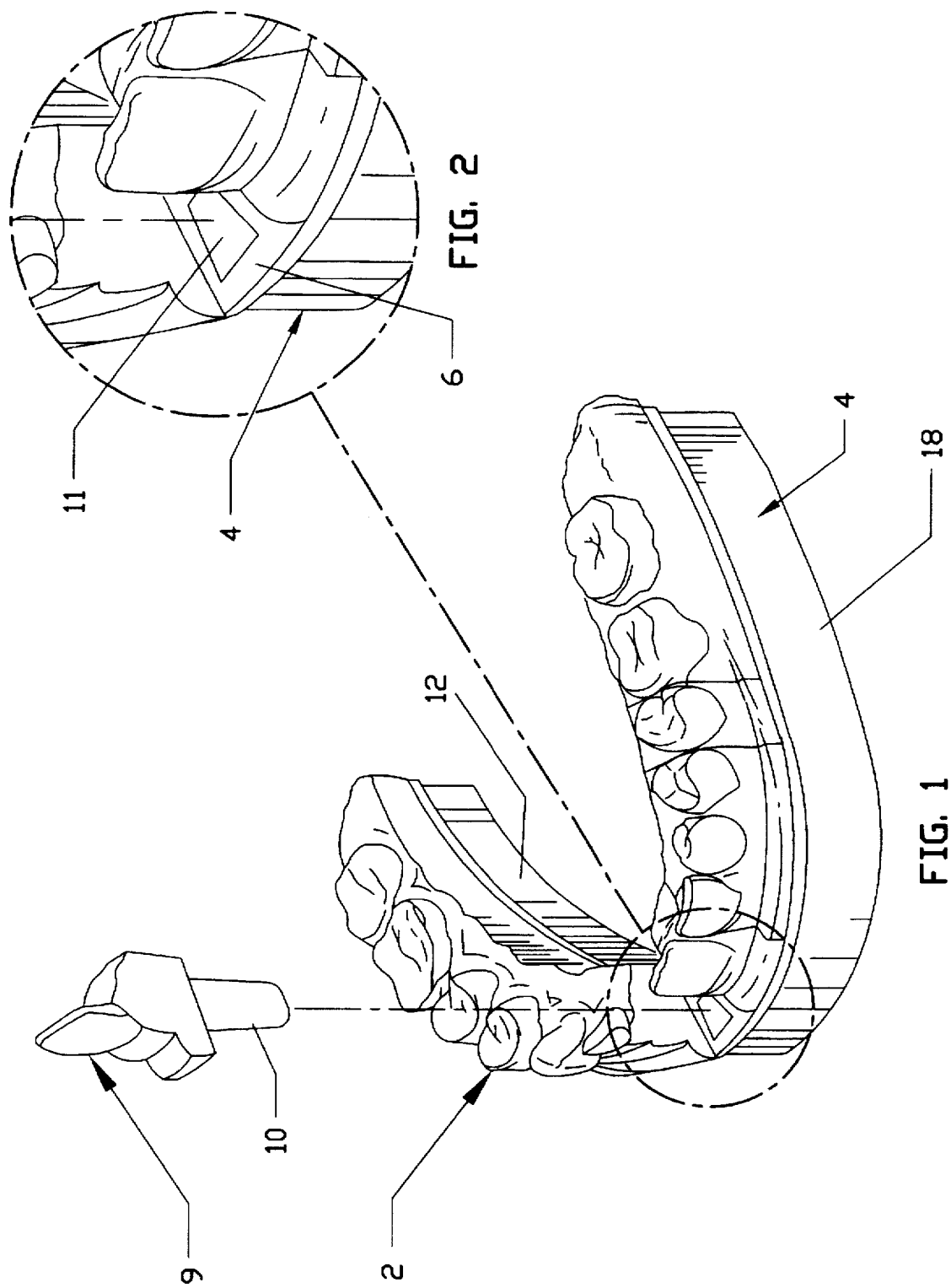

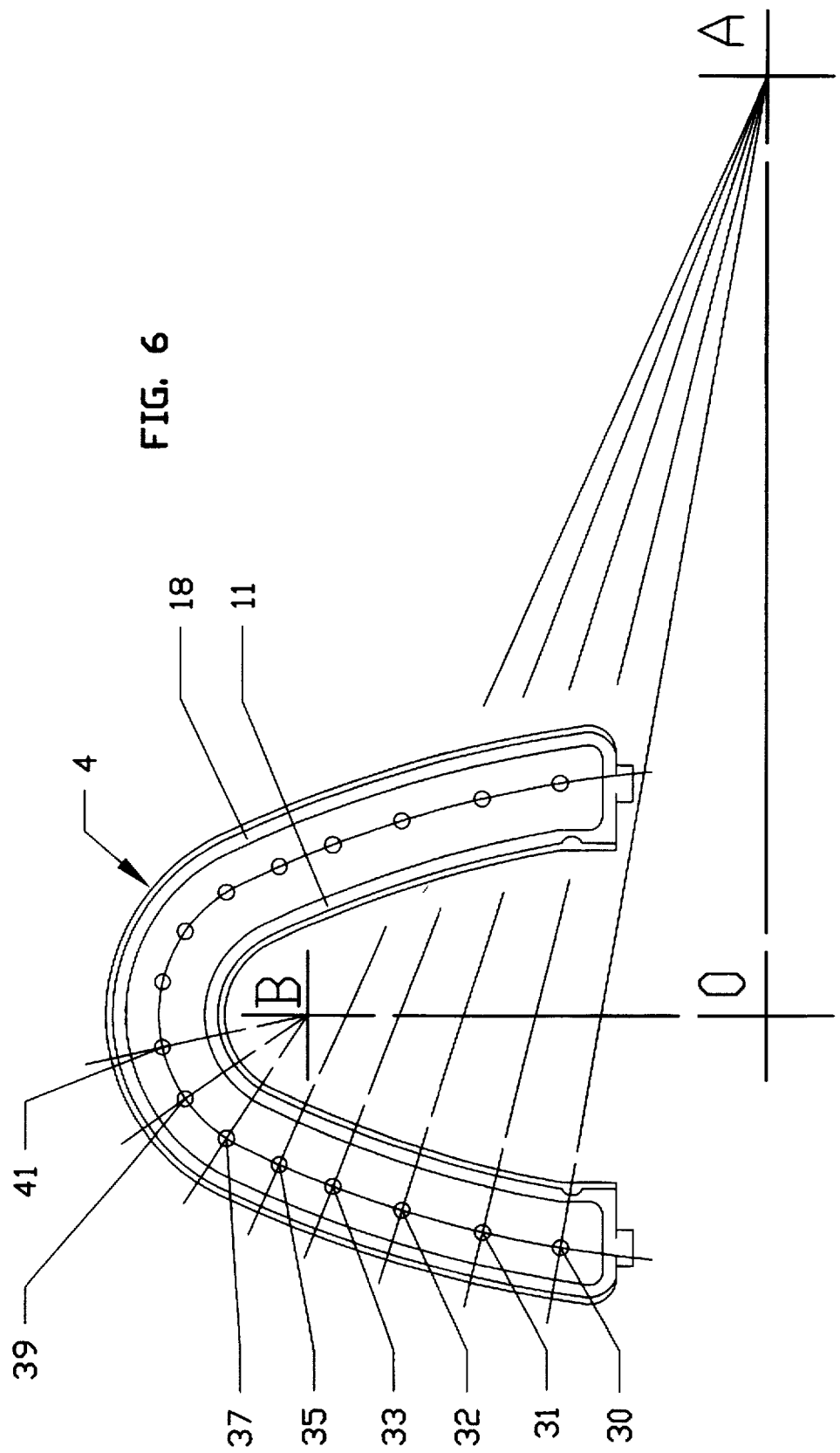

DENTAL MODEL BASE AND METHOD FOR FORMING STONE DOWELS

BACKGROUND

This invention relates generally to a dental model base, and more particularly, to a premanufactured base having a plurality of apertures that are adapted to form stone dowels which support a dental model.

Damaged teeth may be repaired or replaced by crowns, bridge inlays or other common dental prosthesis. A successful repair requires accurate alignment and visual uniformity of the repaired tooth with the patient's other teeth. Typically, a model is made of the patient's teeth and the prosthesis is fitted to the model and adjusted to achieve proper alignment and visual uniformity.

The model is typically formed by having a patient bite into a pliant casting material which cures to create a mold cavity having a negative impression of the patient's teeth and gums. The mold can be of all or any portion of the patient's gum line. A castable material is then poured into the negative impression to create a stone replica or dental model of the patient's teeth and gums.

To facilitate prosthesis development, the replica of the damaged tooth or teeth is severed from the remainder of the dental model. Severability is achieved by positioning the knurled end of a tapered dowel pin in the uncured stone material in correspondence with the damaged tooth or teeth. The dowel pin or pins must be carefully aligned and held in position which requires skill and time. Once the casting of the gum and teeth has hardened, the cured dental model is positioned adjacent an uncured dental model base which is held in a dental base mold. The tapered portion of the dowel pins protruding from the dental model are positioned in the uncured dental model base. To prevent bonding with the dental model base, wax may be placed between the base and the dental model and around the tapered portion of the dowel pins.

Once the dental model base has cured, a saw cut on each side of the damaged tooth model is made down to the dental model base which allows removal of the damaged tooth model and the attached dowel from the rest of the dental model. Once the damaged tooth model is removed, the prosthesis can be fitted and adjusted without the spacial limitations encountered when the damaged tooth model is joined to the full dental model. After the prosthesis is made and attached to the dental model segment, the tapered dowel attached to the dental model segment is guided into its respective aperture in the dental model base which guides the dental model segment to its position in the dental model. Alignment and visual conformity are then assessed.

Alignment is ascertained by evaluating the registration of the repaired tooth with the dental model of the patient's opposing teeth. This is achieved by connecting the upper and lower dental model with an articulator. If the prosthesis is out of alignment or does not visually conform to the rest of the patient's teeth, the dental model segment containing the damaged tooth can be removed, adjusted and returned to the dental model base. This process is repeated until proper alignment and visual conformity is achieved. Thus, the model of the damaged tooth may be removed and inserted into the base repeatedly.

The above described process requires time for the dental model and dental model base castings to cure. Also, skill and time are both required to accurately place the dowel pins in the dental model. Any misalignment may result in an unusable casting. Thus, considerable time is spent achieving proper alignment and allowing the dental model base casting to cure.

Some dental model bases are fabricated from plastic. In one version, a technician must drill a tapered aperture in the dental model base to accommodate the placement of the dowel pin in the dental model casting. Skill and time are required to align the dowel pin with the damaged tooth model and the plastic base and to accurately drill the tapered aperture which receives the tapered dowel pin.

Another available plastic dental model base has a plurality of pre-formed apertures for receiving dowel pins which eliminate the above-mentioned drilling step. However, the apertures are not positioned to correspond with normal tooth placement. Thus, skill is required to accurately align the dowel pins with the dental model.

Also, in existing full arch plastic bases, plastic extends from the right molars to the left molars, creating a platform for excess casting material in the lingual area. It may be desirable to remove this excess casting material as part of the model preparation process. The plastic platform interferes with this removal step. The platform may also may assessment of visual conformity.

In summary, the dowel pins may be accurately aligned with the damaged tooth in a cast dental model base; however, the casting procedure takes time and requires skill. Plastic bases avoid the expense of casting a dental model base but may require additional steps, such as drilling, for accurate placement of a dowel within the dental model. If the plastic base has preformed apertures for dowel placement, the apertures do not correspond to normal tooth placement and skill is required to accurately place the dowels within the dental model. Inaccurate placement of the dowel in a cast or preformed dental model base may result in an unusable dental model as the dental model segment may be unseverable from the dental model.

As mentioned above, metal dowels are typically used to detachably engage a dental mold segment to the dental model base. However, metal dowels are undesirable in some circumstances. For example, porcelain facings are often created to repair damaged teeth. The green porcelain material is applied to a damaged tooth model and the dental model segment containing the tooth model is heated to set the porcelain material. The porcelain heating temperature is elevated and will adversely affect typical metal dowels.

Therefore, what is needed is a preformed dental model base having preformed apertures. An improved base would have apertures corresponding to normal tooth placement. Such a base would eliminate the need to pour a dental model base while reducing the skill and time required to accurately align the dowels within the dental model. Removal of the platform in the lingual area would be an additional improvement, giving technicians improved access to the dental model, facilitating removal of excess casting material in the lingual area and enhancing assessment of visual conformity. Still another improvement would provide a dental model base adapted for supporting a dental model while permitting the disengageable connection of a dental model segment to the dental model base without using metal dowels.

SUMMARY

The present invention is directed to an apparatus that satisfies the need for a preformed dental model base. In one embodiment, the base has a plurality of apertures adopted to form a dowel from the dental model casting material that can detachably connect a dental model segment to the dental model base. In yet another embodiment, the preformed apertures in the dental model base body correspond to normal tooth placement.

The dental model base comprises a premanufactured dental model base body. The base body has a plurality of performed apertures that extend from a dental model support surface into the dental model base body. The preformed apertures have a cross-section adapted for forming and detachably engaging a stone dowel. In another embodiment, a method for using a dental model base is provided. The stone dowels are of sufficient cross-sectional area to resist fracturing under normal conditions and may be repeatedly disengageably connected to the dental model base. Some advantages provided by these embodiments are:

1. Time savings resulting from not casting the dental base;
2. Preformed apertures corresponding to normal tooth placement eliminate the need for proper pin placement in the dental model, thereby saving time and requiring less skill;
3. A full arch base body having a convenient U-shape which allows for removal of excess casting material in the lingual area, improves access to the dental model and enhances assessment of visual conformity;
4. Durable stone dowel/dental base mating surfaces assuring proper alignment with repeated use;
5. A shape corresponding to the normal shape of a patient's gum line;
6. A transparent base that aids assessment of visual conformity;
7. A rigid plastic base that helps minimize shrinkage of the cast dental model; and
8. A dental model base body adapted for forming stone dowels, thereby eliminating the need for metal dowels.

Other advantages and features will become apparent from the following description and from the claims.

BRIEF DESCRIPTION OF THE DRAWINGS

FIG. 1 is a perspective view of a full arch dental model base according to the present invention.

FIG. 2 is an enlarged view of a portion of the full arch dental model of FIG. 1.

FIG. 6 is a plan view of a more detailed aspect of one feature of the present invention.

DESCRIPTION OF THE PREFERRED EMBODIMENTS

Figure 3:
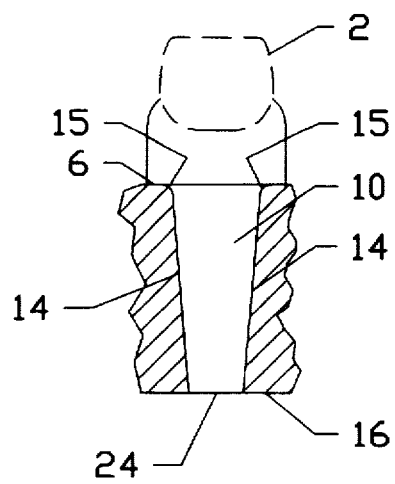
FIG. 3 is a cross-sectional view of the dental model base body of FIG. 1 supporting a dental model according to the present invention.

FIG. 1 depicts a full arch dental model 2 supported by one embodiment of a dental model base body 4 according to the present invention. In this embodiment, a clear acrylic plastic is preferred for the dental model base body, however, many other materials may be used. The dental model 2 is adjacent the dental model support surface 6 which defines one surface of the dental model base body 4. Saw cuts through the dental model 2 on either side of the model of a damaged tooth allow removal of a dental model segment 9. The tapered stone dowel 10 is formed as part of the dental model segment 9 and is detachably engaged with a tapered aperture 11 in the dental model base body 4. In this embodiment, the dental model base body 4 has an interior wall 12. The interior wall 12 is U-shaped and the lingual area is unobstructed.

Figure 4:
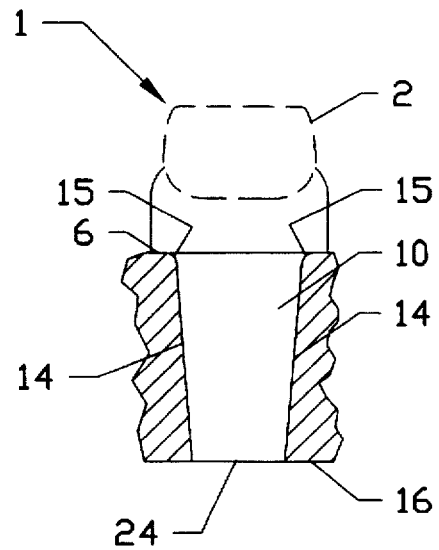
FIG. 4 is a cross-sectional view of a dental model base body of FIG. 1 supporting a dental model according to the present invention.

FIGS. 3 and 4 depict a stone dowel 10 engaging a tapered aperture 11 that extends from the dental model support surface 6 into the dental model base body 4. The tapered aperture has planar side walls 14. The planar side walls 14 intersect the dental model support surface 6 at curved shoulders 15. The stone dowel 10 is tapered such that the cross-sectional area of the stone dowel 10 is greatest at the dental model support surface 6 and decreases as the stone dowel 10 extends into the dental model base body 4. The tapered stone dowel 10 corresponds to the shape of the aperture 8, and thus facilitates insertion and removal of the stone dowel 10 from the aperture 8.

The tapered stone dowel 10 maintains the general spacial relationship of the dental model segment 9 relative to the dental model 2. The noncircular configuration of the stone dowels 10 depicted in this embodiment maintains the orientation of the dental model segment 9 about the axis of the aperture 8. Indexing protrusions (not shown, but see copending application Ser. No. 08/482,738 for a more specific description) may extend from the dental model support surface 6 into the dental model 2 to maintain the proper orientation of the dental model segment 9 about the axis if a tapered circular stone dowel (not shown) is used. The indexing protrusions can be of any configuration sufficient to maintain alignment of the dental model segment 9.

The dental model base body 4 has a first surface 16, an exterior wall 18 and an interior wall 11. The first surface 16 is generally parallel with the dental model support surface 6 and is perpendicular to the interior and exterior walls 12 and 18. The exterior wall 18 intersects the first surface 16. The stone dowels 10 preferably, but not necessarily, extend through the dental model base body 4 but, preferably, do not extend beyond the first surface 16. This preferable feature facilitates disengagement of the stone dowels 10 by simply applying pressure to the stone dowel first surface 24 while the dowel protection flange 20 protects against inadvertent disengagement of the stone dowels 10. Thus, the dental model segment 9 representing a damaged tooth may be removed by cutting through the dental model 2 on both sides of the damaged tooth model. Pressure is then be applied to the stone dowel first surface 24 to remove the dental model segment 9 from the dental model base body 4.

Figure 5:
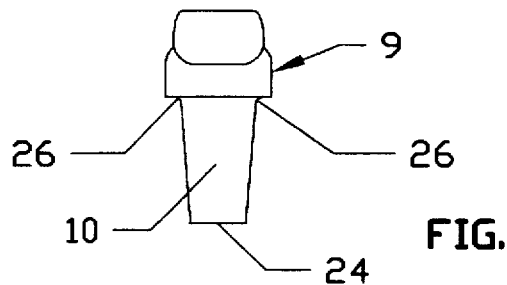
FIG. 5 is a plan view of a dental model segment according to the present invention.

FIG. 5 depicts a dental model segment 9 removed from the dental model base body 4. The gradual transition from the planar side walls 14 to the dental model support surface 6, at the curved shoulders 15, creates an arch 26, which reduces the probability of a fracture between the stone dowel 10 and the dental model 2.

Through analysis of many models, it was discovered that certain geometric relationships exist in the location and arrangement of individuals teeth. This discovery, therefore, permits the arrangement and location of apertures in a model base body to more closely conform to the actual location of teeth in a dental model. It has been determined that the buccal and lingual wall generally tend to have the same curvatures. Teeth are also generally located at the same point along the gum. However, tooth position may vary along the gum if one or more natural teeth are absent or if other abnormalities exist. While the curvature of the buccal and lingual wall remains fairly constant, the size of the gum varies. It has been determined that most gums can be characterized as small, medium or large. The actual location of teeth along a normal gum can be determined by measuring the location of the center of teeth from a sampling of dental models with gums in the desired size range. The measurements are then averaged to determine the average or normal position of teeth in the sample.

FIG. 6 depicts a dental model base body 4 with a designation of the normal placement of the center of upper teeth on a medium-sized gum. The placement of normal teeth along a gum can be defined by certain points, lines, angles and dimensions, as follows. Points A and B are center points for radii useful for designating teeth placement. Line AO is perpendicular to line BO. Point O defines the intersection of lines AO and BO. Line BO bisects the dental model base body 4. Point A is 4.4668 inches to the right of point O. The normal third molar center 30 is found by extending an arc with a 5.6598 inch radius from point A at a 9.75° angle clockwise from line AO and to the left of point A. The normal second molar center 32 is located by extending an arc of a 5.6598 inch radius from point A at a 13.5° angle clockwise from line AO and to the left of point A. The normal first molar center 34 is located by extending an arc with a 5.6598 inch radius from point A at an angle of 17.5° clockwise from line AO and to the left of point A. The normal second bicuspid center 36 is found by extending an arc with a 5.6598 inch radius from point A at a 21° angle clockwise from line AO and to the left of point A. The normal first bicuspid center 38 is found by extending an arc with a 5.5698 inch radius from point A at a 23.75° angle clockwise from line AO and to the left of A. Point B is 2.1443 inches up from point O along line BO. The normal cuspid center 40 is found by extending a 0.7054° inch radius from point B at an angle of 123 clockwise from and to the left of line BO. The normal lateral incisor center 42 is found by extending a 0.7054° inch radius from point B at a 145 angle clockwise from and to the left of line BO. The normal central incisor center 44 is found by extending an arc of a length of 0.7054 inches from point B at a 167° angle clockwise from and to the left of line BO.

These dimensions define the placement of apertures for the left side of a full arch dental model base body 4. The right side of a full arch dental model base body 4 is a mirror image of the left side; therefore, the same geometric relationship will be used to define aperture placement on the right side as well.

Figure 7:
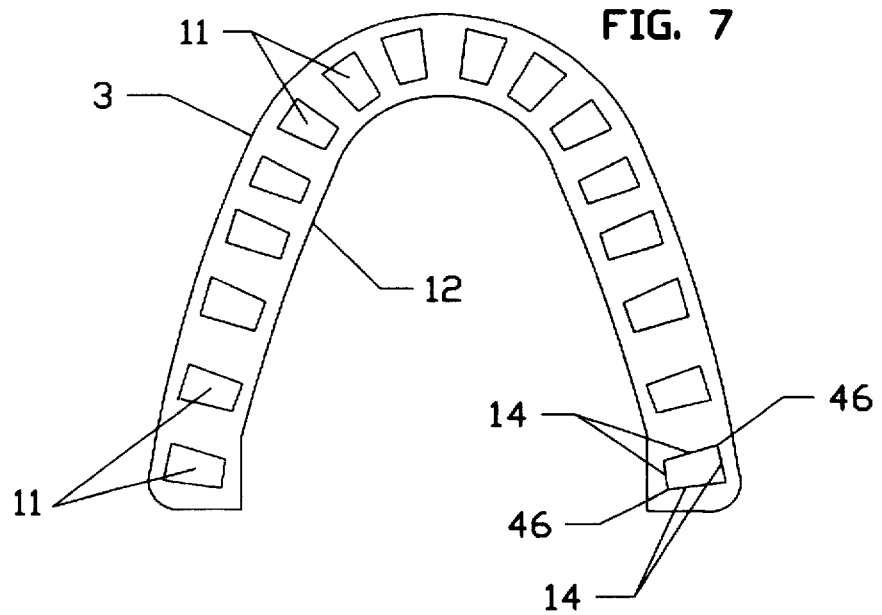
FIG. 7 is a plan view of one embodiment of the present invention.

The exterior wall 18 is located approximately ¼ inches beyond the centerline of the teeth as defined above. The interior wall 11 is located approximately 5/16 inches to the interior of the centerline of the teeth as defined above. As shown in FIG. 7, the apertures 11 are positioned in the dental model base 4 to correspond generally with normal tooth placement. The apertures 11 have planar side walls 14 that are gradually tapered such that the apertures 11 have a greater cross section at the dental model support surface 6 than at the first surface 16. The apertures 11 have a cross-sectional area near the dental model support surface 6 of about 0.03 square inches. In this embodiment, the planar side walls 14 intersect at curved corners 46.

The various aspects of the present invention may be used in the following manner. A dental technician may take a dental model base body according to the present invention and align it with the negative mold of a patient's teeth and gum line. If the patient's teeth correspond to normal tooth placement, the apertures 8 within the dental model base body will generally align with the patient's teeth.

The negative impression is filled with casting material and the dental model base body 4 is brought adjacent the uncured dental model 2. The technician may choose to place wax or some other nonadhesive material between the damaged tooth segment 9 and the dental model base body 4 to reduce adhesion of the damaged dental model segment 9 and the dental model base body 4. The dental model body 4 is the aligned adjacent the uncured dental model and casting material is flowed into the apertures 11. Casting material from the uncured dental model may be flowed into the apertures 11 by gently pressing the dental model base body 4 into the uncured dental model 2 while vibrating the dental model mold. Alternatively, casting material may be introduced in the apertures 11 at the first surface 16. The apertures 11 corresponding to the damaged teeth should align generally with the center of the damaged teeth.

The dental model 2 may be sawed on either side of a damaged tooth, as shown in FIG. 1. The saw-cut extends to the dental model support surface 6. Once the saw-cut has been completed, the dowels 10 supporting the dental model segment 9 of the damaged tooth can be removed by applying pressure to the stone dowel first surface 24 to remove the dental model segment 9. Once the dental model segment 9 is removed, a prosthesis can be prepared to repair the damaged tooth. After the prosthesis is attached to the dental model segment 9, the dental model segment 9 can be returned to its place in the dental model 2. The dowels 10 align the dental model segment 9 generally with the dental model 2.

Once the dental model segment 9 has been returned to the dental model 2, the dental model base body 4 may be attached to an articulator as described in co-pending application Ser. No. 08/482,738 and registration is evaluated. The technician can also determine whether the prosthesis conforms visually to the complete dental model 2. If visual conformity is not achieved or if registration or alignment is improper, the dental model segment 9 containing the damaged tooth and prosthesis can be removed and the technician can adjust the prosthesis accordingly. This process is repeated until proper alignment and visual conformity is achieved.

The foregoing describes various embodiments of the claimed invention. The claimed inventions are not limited to the embodiments described above. For example, it is contemplated that the principles of the invention described above can be applied to half arch dental model bases and quadrant dental model bases. Moreover, numerous alternative constructions exist that would fall within the claimed invention.

What is claimed is:

1. A dental model assembly comprising:
   a dental model formed from a casting material;
   a premanufactured dental model base body adjacent said dental model, said dental model base body having a dental model support surface;
   at least one aperture extending into said dental model base body from said dental model support surface; and
   a stone dowel extending into each said aperture, said stone dowel formed from said casting material and being integral with said dental model.

2. The dental model assembly of claim 1, wherein said aperture is noncircular.

3. The dental model assembly of claim 1, wherein:
   said aperture is tapered, having its greatest cross-sectional area at said dental model support surface.

4. The dental model assembly of claim 1, wherein:
   said dental model base body is adapted to support a full arch dental model.

5. The dental model assembly of claim 4, wherein:

said dental model base body has an interior wall defining an unobstructed lingual area.

6. The dental model assembly of claim 1, additionally comprising:

a plurality of apertures extending into said dental model base body from said dental model support surface, said apertures located to correspond with normal tooth placement.

7. The dental model assembly of claim 1 wherein:

said stone dowel has an arch adjacent said dental model support surface and said aperture.

8. A dental model assembly comprising:

a premanufactured dental model base, said base having a dental model support surface; an aperture extending from said support surface into said base, said aperture located at a predetermined position on said support surface;

a dental model adjacent said support surface, said dental model formed by flowing a casting material into a dental impression; and a stone dowel substantially filling said aperture, said stone dowel formed from flowing said dental model casting material into said aperture, said stone dowel adapted for detachably engaging a cut section of said dental model with said dental model base.

9. A method for making a dental model, comprising the steps of:

flowing a casting material into a mold having a negative impression of a patient's teeth;

placing a premanufactured dental model base body adjacent said mold, said dental model base body having a dental model support surface adjacent said casting material in said mold, said dental model base body having an aperture extending from said dental model support surface into said dental model base body; and flowing said casting material into said aperture.

10. The method of claim 9, wherein:

said dental model base body has a first surface remote from said dental model support surface, said aperture extending from said dental model support surface through said dental model base body to said first surface and said casting material is flowed into said aperture from said dental model support surface.

11. The method of claim 9, wherein:

said aperture is tapered having a greatest cross-sectional area at said dental model support surface.

12. The method of claim 9, wherein:

said aperture is noncylindrical.

13. The method of claim 9, wherein:

said aperture has a noncircular cross-section.

14. The method of claim 9, wherein:

a protrusion extends from said first surface into said dental model located a predetermined distance from said aperture.

15. The method of claim 9, wherein:

said aperture extends from said support surface through said dental model base body.

16. The method of claim 9, wherein:

said dental model has a plurality of apertures extending into said dental model base body from said dental model support surface, said apertures located to correspond with normal tooth placement.

* * * * *

UNITED STATES PATENT AND TRADEMARK OFFICE
CERTIFICATE OF CORRECTION

PATENT NO. : 5,788,490

DATED : AUGUST 4, 1998

INVENTOR(S) : HUFFMAN

It is certified that error appears in the above-identified patent and that said Letters Patent is hereby corrected as shown below:

Col. 2, line 19: "may also may" should read —may also hinder—

Col. 5, line 56: "comers" should read —corners—

Signed and Sealed this

Sixth Day of June, 2000

Attest:

Q. TODD DICKINSON

*Attesting Officer*   *Director of Patents and Trademarks*